United States Patent
Zhang et al.

(10) Patent No.: US 11,135,160 B2
(45) Date of Patent: Oct. 5, 2021

(54) USE OF CHLOROGENIC ACID IN PREPARING PHARMACEUTICALS FOR TREATMENT OF LAG-3-MEDIATED DISEASE

(71) Applicant: SICHUAN JIUZHANG BIOLOGICAL SCIENCE AND TECHNOLOGY CO. LTD, Sichuan (CN)

(72) Inventors: Jie Zhang, Sichuan (CN); Xiaoguang Chen, Sichuan (CN); Nina Xue, Sichuan (CN); Mengtian Zhang, Sichuan (CN)

(73) Assignee: SICHUAN JIUZHANG BIOLOGICAL SCIENCE AND TECHNOLOGY CO., LTD, Sichuan (CN)

( * ) Notice: Subject to any disclaimer, the term of this patent is extended or adjusted under 35 U.S.C. 154(b) by 0 days.

(21) Appl. No.: 16/085,392

(22) PCT Filed: Feb. 20, 2017

(86) PCT No.: PCT/CN2017/074065
§ 371 (c)(1),
(2) Date: Sep. 14, 2018

(87) PCT Pub. No.: WO2017/157131
PCT Pub. Date: Sep. 21, 2017

(65) Prior Publication Data
US 2019/0175499 A1 Jun. 13, 2019

(30) Foreign Application Priority Data
Mar. 15, 2016 (CN) .......... 201610149050.5

(51) Int. Cl.
*A61K 9/00* (2006.01)
*A61K 31/216* (2006.01)
(Continued)

(52) U.S. Cl.
CPC .............. *A61K 9/0065* (2013.01); *A61K 9/16* (2013.01); *A61K 9/20* (2013.01); *A61K 9/2009* (2013.01);
(Continued)

(58) Field of Classification Search
CPC ....... A61K 9/16; A61K 9/2018; A61K 9/2009
See application file for complete search history.

(56) References Cited

U.S. PATENT DOCUMENTS

| | | | | |
|---|---|---|---|---|
| 2002/0110606 A1* | 8/2002 | Graus | ................. | A61K 31/192 424/728 |
| 2006/0034918 A1* | 2/2006 | Messadek | ............ | A61K 9/0065 424/464 |

FOREIGN PATENT DOCUMENTS

| | | |
|---|---|---|
| CN | 102391119 A | 3/2012 |
| WO | 2009091134 A2 | 7/2009 |

* cited by examiner

*Primary Examiner* — San Ming R Hui
(74) *Attorney, Agent, or Firm* — Novick, Kim & Lee, PLLC; Allen Xue

(57) ABSTRACT

Provided are a use of chlorogenic acid in preparing pharmaceuticals for the inhibition of LAG-3 and a use of chlorogenic acid in preparing pharmaceuticals for the treatment of LAG-3-mediated diseases. The inhibition of LAG-3 by chlorogenic acid is useful in cancer therapy, anti-viral therapy, and sepsis treatment. The oral bioavailability of chlorogenic acid is enhanced by preparing chlorogenic acid as a gastric floating tablet.

4 Claims, 9 Drawing Sheets

Specification includes a Sequence Listing.

(51) Int. Cl.
*A61K 9/20* (2006.01)
*A61P 31/20* (2006.01)
*A61P 35/02* (2006.01)
*A61P 31/04* (2006.01)
*A61P 35/00* (2006.01)
*A61K 9/16* (2006.01)
*C07C 69/732* (2006.01)

(52) U.S. Cl.
CPC .......... *A61K 9/2013* (2013.01); *A61K 9/2018* (2013.01); *A61K 9/2054* (2013.01); *A61K 31/216* (2013.01); *A61P 31/04* (2018.01); *A61P 31/20* (2018.01); *A61P 35/00* (2018.01); *A61P 35/02* (2018.01); *C07C 69/732* (2013.01)

USE OF CHLOROGENIC ACID IN PREPARING PHARMACEUTICALS FOR TREATMENT OF LAG-3-MEDIATED DISEASE

INCORPORATION OF SEQUENCE LISTING

This application contains a sequence listing submitted in Computer Readable Form (CRF). The CFR file containing the sequence listing entitled "PA288-0025-sequence-txt.txt", which was created on Jan. 31, 2019, and is 821 bytes in size. The information in the sequence listing is incorporated herein by reference in its entirety.

TECHNICAL FIELD

The present invention belongs to the technical field of bio-medicine, and in particular, relates to the use of chlorogenic acid in preparing pharmaceuticals for the treatment of LAG-3-mediated disease.

BACKGROUND ART

Chlorogenic acid (CA), also called caffeotannic acid, is a phenolic acid formed by condensation of caffeic acid and quinic acid, with a chemical name of 3-o-caffeoylquinic acid (CA).

Chlorogenic acid is a phenylpropanoid compound synthesized by intermediate products in pentose phosphate pathway during aerobic respiration process of plants. Chlorogenic acid has already been developed and used in many fields such as food, health care, cosmetics, medicine, and so on. As a natural small-molecule pure compound originated from plants, the previous investigation indicated that chlorogenic acid possesses extensive biological activities such as anti-oxidant, anti-inflammatory, anti-virus, anti-tumor, etc., but its playing above roles by acting on which target points has not been well documented by now. Finding the action targets of chlorogenic acid, clarifying the pathway of this target, and correspondingly regulating this site have a great importance for further wide use and precision treatment of chlorogenic acid.

Lymphocyte activating gene 3 (LAG-3), also named CD233, is a cell membrane protein belonging to immunoglobulin super family, and a inhibitory molecule expressed on T lymphocyte surface. Research indicated that LAG-3 plays an important role in regulating T cell function, and takes part in the regulation of generation and activation of T lymphocytes and effector T lymphocytes, as well as is related to immune dysfunction at various morbid states. Development of drugs with LAG-3 as target may have a wide application prospect.

SUMMARY OF THE INVENTION

In order to resolve the problems existed in the prior art, the object of the present invention is to provide a use of chlorogenic acid in inhibiting LAG-3 target.

The present invention discloses the use of chlorogenic acid as the inhibitory agent of LAG-3 target. In the present invention, chlorogenic acid can obviously act on the LAG-3 target, have an inhibitory effect on the content and the expression of LAG-3 target, and inhibit the corresponding gene, mRNA, and protein of LAG-3, thus can be used for treatment of corresponding disease.

LAG-3 has a close relationship with the tumor, and it has been shown that LAG-3 has an inhibition on lymphocytes $CD4^+T$ and $CD8^+T$, thus producing the immune tolerance of tumors, as well as promoting the growth and development of tumors. Therefore, inhibiting LAG-3 has become an advancing research for antitumor immunotherapy. LAG-3 is also closely related with the virus, and the pathologic mechanism of chronic hepatitis B is mainly an immunopathogenesis reaction. HBV persistent infection has a direct relationship with the response hypofunction of lymphocytes, and LAG-3 is related with the progression of chronic hepatitis B disease, thus inhibiting LAG-3 of patients with chronic hepatitis B disease will have a positive action on the disease. Similarly, LAG-3 also has a relationship with sepsis, and sepsis is a disease of inflammatory reaction and immune response due to body allergy caused by a series of factors such as trauma, infection, etc., and then has a significant damage to the body, with a very high mortality. Its pathogenetic process is closely related to the inhibition of immune function, and the recent investigation indicated that the high expression of LAG-3 in T-lymphocytes of patients with sepsis is correlated with the bad prognosis of this disease. Inhibiting LAG-3 may be a new idea for treatment of sepsis.

Previous study (including the example study in the patent) has already identified that chlorogenic acid can promote the generation of lymphocyte CD4+T in experimental mice, and in the process of researching and exploring the indications of chlorogenic acid, it has been shown that chlorogenic acid has potent therapeutic value for various diseases. Based on the fact that chlorogenic acid acts on lymphocyte CD4+T and the corresponding indications of chlorogenic acid, the inventors gradually narrow the research scope, and finally, validate the fact that chlorogenic acid acts on the LAG-3 target and inhibits the expression of LAG-3 by lots of in vivo and in vitro experiments, as well as chlorogenic acid, as a drug, is used for treatment of related diseases with LAG-3 as target point.

Chlorogenic acid itself is a natural product existing in the nature, and the inventors first use chlorogenic acid as medicinal monomer in clinical trials in the world (currently, the experimental trials are in progress, with a clinical trial permission number 2013L01855). Chlorogenic acid has wide biological activities, and its effective pathways are very numerous, thus it is needed to clarify its true action targets, so as for determining its possible application direction, screening out the population group suitably using chlorogenic acid, and reversely advancing the research progress of certain diseases with unknown pathologic mechanism.

Previous drug development is mostly based on the premise that the disease has a known pathogenesis, and according to the pathologic mechanism, the drug related with the mechanism is artificially synthesized and used for treatment of related diseases. But chlorogenic acid is an old agent existing in the biosphere, and not suitable to the above development model, since under the conditions of not understanding its action mechanism, lots of research has been carried out, and at last, the close relationship of chlorogenic acid and LAG-3 is confirmed, that has a very important value.

By investigation, the inventors find that chlorogenic acid can directly act on the LAG-3 target, and inhibit the expression of LAG-3 and LAG-3 protein, thus treat the diseases with LAG-3 as target, including malignant tumors, infection viral diseases, and sepsis. By researching, it is shown that in the cell lines highly expressing LAG-3, chlorogenic acid can obviously act on the LAG-3 target, and produce an inhibitory effect; the drug containing chlorogenic acid can obviously reduce the LAG-3 expression rate in peripheral blood lymphocytes of model mice. Moreover, chlorogenic acid can obviously promote the proliferation of lymphocytes CD3+T and CD4+T, inhibit the expression of LAG-3 protein in tumors, and thus produce therapeutic effects on tumors. In addition, chlorogenic acid can obviously lower the content of alanine aminotransferase (ALT) in blood, and thus produce therapeutic effects on infection viral diseases. Chlorogenic acid can also treat sepsis related with LAG-3 by inhibiting LAG-3 target.

In the present invention, preferably, said drug can be a preparation prepared by chlorogenic acid as active ingredient, with addition of pharmaceutically acceptable adjuvants or auxiliary components.

In particular, said preparations of the present invention are preferably gastric floating tablets or powder. Amongst, gastric floating tablets are prepared by using chlorogenic acid as principal agent, hydroxypropyl cellulose as backbone materials, stearic acid as floating assistant, sodium bicarbonate as foaming agent, as well as microcrystalline cellulose and lactose as bulking agent, and thus further improve the oral bioavailability of chlorogenic acid, so as to produce more obvious therapeutic effects on the diseases with LAG-3 as target.

Compared with the prior art, the present invention shows that chlorogenic acid has an inhibitory effect on the LAG-3 target, and is further used for treatment of diseases with LAG-3 as target, such as anti-tumor, anti-virus, sepsis, etc; further, chlorogenic acid can be prepared as gastric floating tablets by suitable methods, for further improving the oral bioavailability of chlorogenic acid.

EXAMPLES

Figure 1:
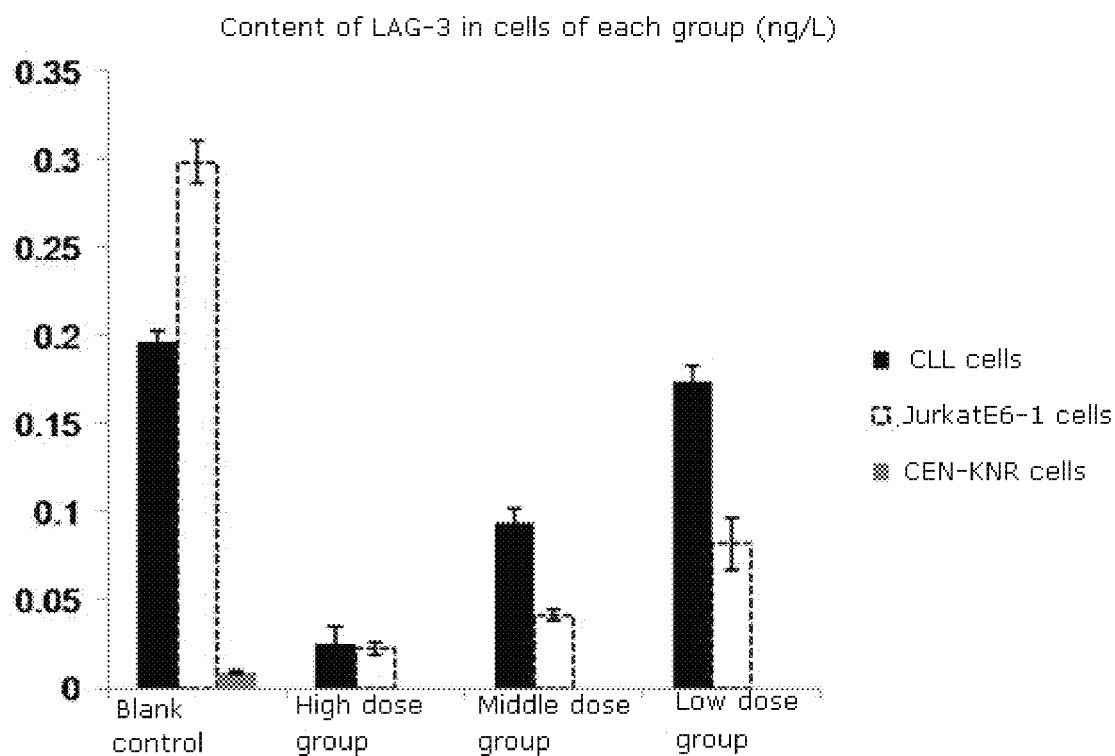
FIG. 1 shows the content detection result of LAG-3 in cells of each group in example 1.

In the present specification, all disclosed features or all disclosed methods or steps in the process, unless mutually exclusive features and/or steps, can be combined in any way.

Any feature disclosed in the present specification, unless particularly indicated, can be replaced by other equivalent or alternative feature with same purpose, i.e. unless particularly indicated, each feature is only an example of a series of equivalent or same features.

[Example 1] Investigation on the Effect of Chlorogenic Acid on the High-Expressed Lymphocyte Activation Gene 3 (LAG-3) Cell Lines 1. Experimental Materials
1.1 Cell Lines
CLL cells human chronic lymphocytic leukemia cells
JurkatE6-1 human T lymphocytic leukemia cells
CEM-NKR human lymphoma cells
1.2 Experimental Drugs, Kits and Apparatus
Crude drug chlorogenic acid with a purity of 99.2%, extracted from *Folium eucommiae* leaves; cell culture dish; carbon dioxide incubator; RNA prep Pure cultured cell/bacteria total RNA extraction kit; cDNA first strand synthesis kit; fluorescent quantitation PCR apparatus; human lymphocyte activation gene 3 detection kit; ELISA, etc.
2. Experimental Method and Detection Index
2.1 Cellular Process
CLL cells and JurkatE6-1 cells in exponential phase of growth with good conditions were inoculated in 6 well plate at a concentration of $5\times10^5$/ml. Each kind of cells were set four groups, and each group has three repeat holes for administration. Amongst, three chlorogenic acid groups received the drug dissolved in blank 1640 medium (1 mL) at the desired concentration, while the blank control group received the same volume of blank 1640 medium. The detailed groups and the dose schedule are shown in Table 1.

TABLE 1

Experimental groups, dosage, and the administration time of Example 1

| Cells | Groups | Drug concentration (μM) | Drug action time (h) |
|---|---|---|---|
| CLL cells | Blank control group (CB) | 0 | 48 |
|  | High dose group of chlorogenic acid (CHCA) | 100 |  |
|  | Middle dose group of chlorogenic acid (CMCA) | 50 |  |
|  | Low dose group of chlorogenic acid (CLCA) | 10 |  |
| Jurkat cells | Blank control group (JB) | 0 | 48 |
|  | High dose group of chlorogenic acid (JHCA) | 100 |  |
|  | Middle dose group of chlorogenic acid (JMCA) | 50 |  |
|  | Low dose group of chlorogenic acid (JLCA) | 10 |  |
| CEM-NKR cells | Blank control group (CNB) | 0 | 48 |

2.2 Determination of LAG-3 Activity Using Human Lymphocyte Activation Gene 3 Detection Kit In this example, by ELISA experiment, the activity of LAG-3 in cells of each group was determined using human lymphocyte activation gene 3 detection kit. After cells of each group acted with corresponding drugs for 48 h, cell culture fluid of each group was collected and divided into two parts. The protein of one part was quantitated using BCA method, and the activity of LAG-3 in cells of each group was determined using human lymphocyte activation gene 3 detection kit, to calculate the content of LAG-3 in each group.

2.3 Determination of the Expression of LAG-3 Gene in Cells of Each Group Using RT-PCR Method (1) Extraction of Total RNA in Cells Using RNA prep Pure cultured cell/bacteria total RNA extraction kit (centrifugal column), total RNA was extracted from cells, and the operative procedures were carried out as the instructions. The detailed extraction procedures are briefly described as follows:

1) Another cell culture fluid remained in step 2.2 after equally dividing was taken out, to which was added 200 µl lysate RL with pre-added β-mercaptoethanol;

2) The above liquid was centrifuged for 5 min at 12,000 rpm, and the supernatant fluid was carefully suctioned for use;

3) To the supernatant fluid, was slowly added 0.5 time volume of absolute ethanol, and after mixed thoroughly, the solution was transferred to the absorption column CR3, centrifuged for 1 min at 12,000 rpm, then the waste solution was discarded, while the absorption column was kept;

4) Deproteinization solution RW1 was added to the absorption column, to remove the protein, after that, the solution was centrifuged for 1 min, and the waste solution was discarded;

5) DNase I working solution was added, to remove DNA on the column;

6) After the absorption column was washed with the deproteinization solution and the wash solution, respectively, the absorption column was placed in the collection tube, and the residual liquid on it was fully evaporated;

7) To the absorption column, was added 60 µl RNase free ddH$_2$O, after standing for 2 min, the column was centrifuged at 12,000 rpm for 2 min, to obtain the mRNA sample;

(2) Reverse Transcription of mRNA

Using cDNA first strand synthesis kit and the resultant RNA solution by above extraction, the corresponding first strand cDNA was synthesized. The detailed reverse transcription procedures were carried out according to the instructions, that is briefly described as follows:

200 µl enzyme-free centrifuge tube was placed in an ice bath, to which were added the following solutions shown in Table 2:

TABLE 2

The solution and its amount added in the reverse transcription procedures of mRNA in example 1

| | |
|---|---|
| RNA template | 5 mL |
| Oligo(dT)15 | 2 mL |
| Super Pure dNTP | 2 mL |
| RNase-Free ddH2O | 5.5 mL |
| Total | 14.5 mL |

After centrifugation, the centrifuge tube was placed in PCR apparatus, and incubated for 5 min at 70° C. The solution was briefly collected and rapidly transferred to the ice for cooling 2 min, then the reagents shown in Table 3 were supplemented:

TABLE 3

The reagents and their amounts added in the reverse transcription procedures of mRNA in example 1

| | |
|---|---|
| Above-mentioned system | 14.5 mL |
| 5 × first strand buffer (containing DTT) | 4 mL |

TABLE 3-continued

The reagents and their amounts added in the reverse transcription procedures of mRNA in example 1

| | |
|---|---|
| RNasin | 0.5 mL |
| TIANScript M-MLV (200 U) | 1 mL |
| Total | 20 mL |

After the centrifuge tube was gently mixed and briefly centrifuged, the tube was placed in PCR apparatus set at 42° C. for incubating 50 min, and then heated at 95° C. for 5 min. Finally, to the resultant cDNA solution, was added 30 µl RNase-Free ddH$_2$O and then diluted to 50 µl, to obtain the first strand cDNA.

(3) RT-PCR Quantitation

Because EvaGreen fluorescent dye can produce strong fluorescence when binding with the double-stranded DNA, the total amount of DNA formed by reaction can be obtained by detecting the final fluorescence intensity. To the test tube, were added fluorescent dye, cDNA product synthesized in steps (1) and (2), LAG-3 primer (Forward primer SEQ ID NO: 1 5'-CTAGCTAGCAGCGAGCTCCTTCCAGTC-3', downstream primer SEQ ID NO: 2 5'-GACTG-GAAGGAGCTCGCTGCTACGTAG-3'), and well mixed, then subjected to RT-PCR measurement. Amongst, β and w primer group was set for each sample for calculating the relative magnitude, to perform the relative quantitation.

3. Experimental Results 3.1 the Activity Detection Results of LAG-3 in Cells of Each Group Using ELISA method, the content of LAG-3 in cells of each group was determined. The experimental results showed that comparing with CEM-NKR cells in the control group, the content of LAG-3 in CLL cells and JurkatE6-1 cells in the blank group was higher, consistent with that CLL and JurkatE6-1 are cell lines highly expressing LAG-3, as reported in literature. After high, middle, and low doses of chlorogenic acid acted with cells, the content of LAG-3 in CLL cells and JurkatE6-1 cells both lowered, and the reduced degree was correlated with the amount of chlorogenic acid. Amongst, compared with the corresponding CB group (CLL blank control group), the content of LAG-3 in CHCA group (CLL cells in high dose group of chlorogenic acid) and CMCA group (CLL cells in middle dose group of chlorogenic acid) is obviously different (*$p<0.05$); while in JrukatE6-1 cells, compared with the corresponding CB group (JurkatE6-1 blank control group), the content of LAG-3 in JHCA group (JurkatE6-1 cells in high dose group of chlorogenic acid) and JMHC group (JurkatE6-1 cells in middle dose group of chlorogenic acid) is obviously different (*$p<0.05$).

Results showed that chlorogenic acid can obviously inhibit the content of LAG-3 in CLL cells and JurkatE6-1 cells highly expressing LAG-3, as well as the inhibitory effect and the amount of chlorogenic acid were correlated, and the detailed experimental results were shown in FIG. 1. Amongst, high dose group, middle dose group, and low dose group denoted the content of LAG-3 in different cells after treating with high, middle, and low doses of chlorogenic acid, respectively.

3.2 The Detection Result of LAG-3 Gene Expression Level in Cells of Each Group

Using RT-PCR method, LAG-3 gene expression status in cells of each group was determined. Experimental results showed that compared with CEM-NKR cells in the control group, the expression level of LAG-3 gene in CLL cells and JurkatE6-1 cells in the blank group is higher, consistent with that CLL and JurkatE6-1 are cell lines highly expressing LAG-3, as reported in literature. After high, middle, and low doses of chlorogenic acid acted with cells, the expression level of LAG-3 gene in CLL cells and JurkatE6-1 cells both obviously lowered, and the reduced degree was correlated with the amount of chlorogenic acid. Amongst, compared with the corresponding CB group (CLL blank control group), the expression level of LAG-3 gene in CHCA group (CLL cells in high dose group of chlorogenic acid), CMCA group (CLL cells in middle dose group of chlorogenic acid), and CMCA group (CLL cells in low dose group of chlorogenic acid) is obviously different (*p<0.05); while in JrukatE6-1 cells, compared with the corresponding JB group (JurkatE6-1 blank control group), the expression level of LAG-3 gene in JHCA group (JurkatE6-1 cells in high dose group of chlorogenic acid), JMHC group (JurkatE6-1 cells in middle dose group of chlorogenic acid), and JMHC group (JurkatE6-1 cells in low dose group of chlorogenic acid) is obviously reduced, with significant difference (*p<0.05).

Figure 2:
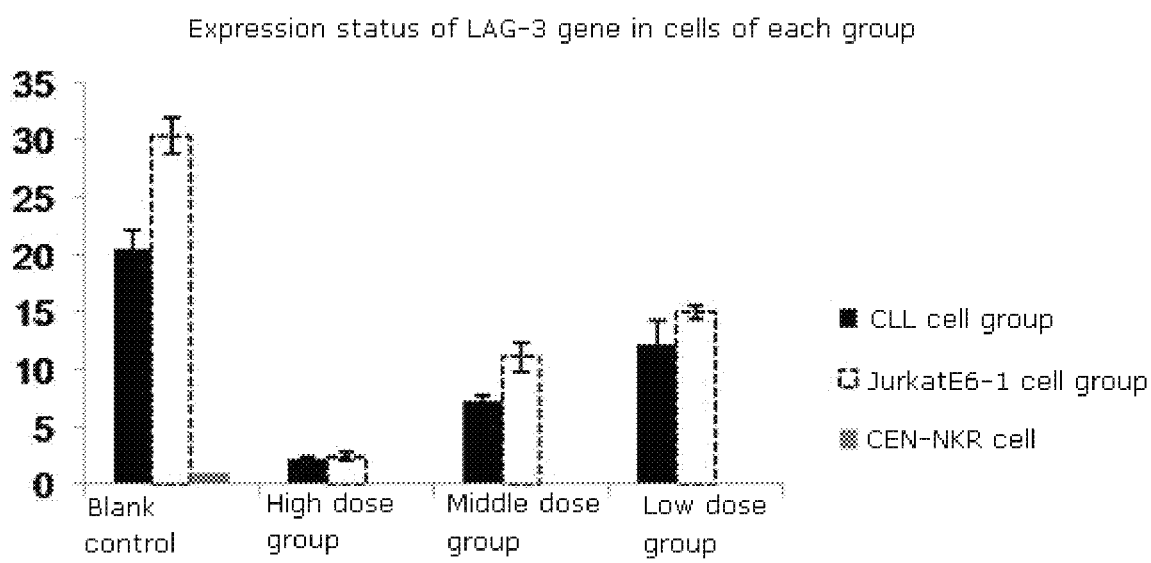
FIG. 2 shows the expression level detection result of LAG-3 gene in cells of each group in example 1.

Results showed that chlorogenic acid can obviously inhibit the expression status of LAG-3 gene in CLL cells and JurkatE6-1 cells highly expressing LAG-3, as well as the inhibitory effect and the amount of chlorogenic acid were correlated, and the detailed experimental results were shown in FIG. 2. Amongst, high dose group, middle dose group, and low dose group denoted the expression level of LAG-3 gene in different cells after treating with high, middle, and low doses of chlorogenic acid, respectively.

In this example, using CLL cells and JurkatE6-1 cells highly expressing LAG-3 as model cells, using CEM-NKR cells as the control cells, the expression level of LAG-3 in cells was directly investigated after treating CLL and JurkatE6-1 cells with chlorogenic acid, and the LAG-3 expression was detected from two aspects, i.e. the content and the gene expression level. Results showed that in cell lines highly expressing LAG-3, chlorogenic acid can obviously act on the LAG-3 target and produce inhibitory effects.

[Example 2] the Regulatory Effect of Chlorogenic Acid Freeze-Dried Powder Injection on the Expression Level of LAG-3 in Mice 1. Experimental Animals and Materials Acute T lymphocyte series leukemia model mice; chlorogenic acid freeze-dried powder injection prepared by chlorogenic acid with a purity of 98.9% that is extracted from *Eucommia ulmoides*; LAG-3-PE antibody; flow cytometer; etc.

2. Experimental Method and Testing Index

Acute T lymphocyte series leukemia model mice were randomly divided into 3 groups, including the saline control group, LAG-3 antibody positive control group, and chlorogenic acid injection group, six mice for each group. According to Table 4, the drug for different group was prepared, and successively intravenously fused for 15 days, then the experiment was completed. The day finishing the first injection was regarded as the first day, and on the sixteenth day, the eyeball of mice was enucleated for sampling blood. After blood sample treatment, lymphocytes were isolated and dyed with LAG-3PE antibody. The expression status of LAG-3 in peripheral blood lymphocytes of each group mice was detected using flow cytometer.

TABLE 4

Experiment groups and dosage regimen in example 2

| Groups | Dose (mg/kg) | Dosing times | Administration mode |
|---|---|---|---|
| Blank control group (group B) | The same volume of saline | 15 | Intravenous injection |
| LAG-3 antibody group (group LAG3Ig) | 5 | 15 | |
| Chlorogenic acid injection group (group CA) | 10 | 15 | |

3. Experimental Results

Figure 3:
FIG. 3 shows the LAG-3 expression level in peripheral blood lymphocytes of each group mice in example 2.
Figure 4:
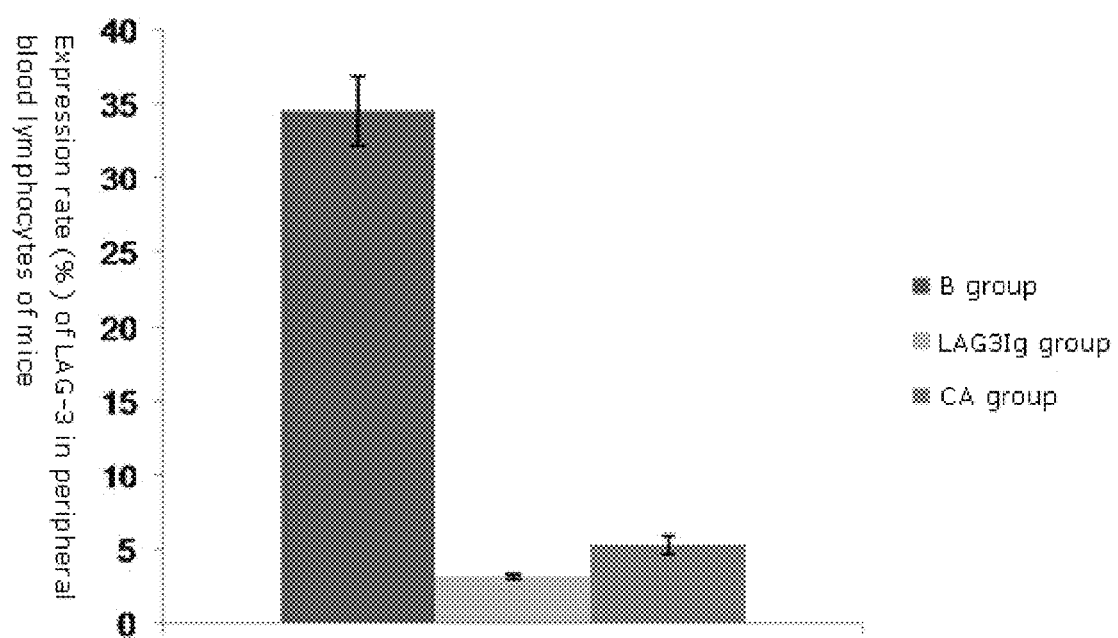
FIG. 4 shows the LAG-3 expression rate (%) in peripheral blood lymphocytes of each group mice in example 2.

After LAG-3 shown in peripheral blood lymphocytes of each group mice was detected using flow cytometer, it was found that compared with the blank control group (Group B), the expression level of LAG-3 in peripheral blood lymphocytes in both LAG-3 antibody group (Group LAG3Ig) and chlorogenic acid injection group (Group CA) was obviously down regulated, and both of groups did not have significant difference (p>0.05). The detailed experimental results were shown in FIG. 3, and the detailed statistical data were shown in FIG. 4.

LAG-3 is inhibitory molecules present in lymphocytes, and in this example, acute T lymphocyte series leukemia mice were used as the model. After treated with chlorogenic acid freeze-dried powder injection, the expression status of LAG-3 in peripheral blood lymphocytes of mice was investigated using flow cytometer. Results showed chlorogenic acid freeze-dried powder injection can obviously reduce the expression rate of LAG-3 in peripheral blood lymphocytes of model mice, with an inhibitory effect close to that of LAG-3 antibody.

[Example 3] Pharmacodynamics Study of Chlorogenic Acid Freeze-Dried Powder Injection Used for Treatment of Malignant Brain Glioma in Mice 1. Experimental Animals and Materials
1.1 Experimental Animals 6-8 weeks female/male C57BL/6 mice (40 mice), weighing 18-21 g, SPF grade.

1.2 Experimental Materials and Apparatus

Flow cytometer; OLYPMPUSPC35DX pathology imaging system and microscope; ELISA; etc.

2. Experimental Method and Testing Indexes
2.1 Preparation of Chlorogenic Acid Freeze-Dried Powder Injection Chlorogenic acid was extracted and purified from *Folium eucommiae* leaves, with a purity of about 99.52%.

50 g chlorogenic acid, 70 g mannitol, and 5 g sodium bisulphite were completely dissolved in the water for injection, filtered, filled, and lyophilized to prepare 50 mg/branch chlorogenic acid freeze-dried powder injection.

2.2 Animal Model Establishment and Dosing Regimen

GL261 glioma cells in exponential phase of growth were prepared as GL261 single cell suspension at a concentration of $5 \times 10^5/\mu L$. After anesthetized with 0.75% pentobarbital sodium at 6 μL/g, the hair at the puncture site was stripped, and the heads of mice were fixed with ALC-H mouse brain stereotactic apparatus for longitudinal incision of scalp. 10 mL GL261 single cell suspension was injected using micro pump at 2.5 μL/min, and the pinpoint was sealed with bone wax, then the incision of scalp was carefully sutured. Totally, 35 mice were inoculated, and the remained 5 mice were normal. The dead mice were removed, and C57BL/6 mice inoculated with GL261 glioma cells were randomly divided to 3 groups, including the saline control group (NC group), chlorogenic acid injection group (CA group), and temozolomide (TMZ) positive control group. Amongst, CA group is intraperitoneally injected with 40 mg/kg chlorogenic acid everyday, NC group is injected with the same volume of saline, and TMZ treatment group orally takes 20 mg/kg temozolomide. The administration was kept for 7 days, and the detailed animal groups and the dose schedule are shown in Table 5.

TABLE 5

The experimental grouping for pharmacodynamics testing of mouse brain in situ glioma in example 3

| Group | Dosage (mg/kg) | Dosing times | Administration mode |
|---|---|---|---|
| Saline control group (NC group) | Same volume of saline | 7 | intraperitoneal injection |
| Chlorogenic acid injection treatment group (CA group) | 40 | 7 | intraperitoneal injection |
| Temozolomide treatment group (TMZ group) | 20 | 7 | Oral administration/ intragastric administration |

2.3 Testing Indexes (1) Pharmacodynamics Investigation on Tumor Size

In order to most intuitively measure the tumor therapy status of mice after different treatment ways, mice were scanned by nuclear magnetic imaging apparatus of small animal, to investigate the in situ tumor size in mouse brain and calculate the tumor volume.

(2) Immunohistochemical Investigation

In order to investigate the expression status of LAG-3 protein in lesion tissues of each group mice and confirm the correlation of LAG-3 and the disease progression, immunohistochemical mode was used in this experiment. The samples including in situ lesion of each group mice, together with the brain tissue of normal mice, were investigated for their expression status of LAG-3 protein.

The detailed operation method was as follows:

After completion of experiment, in situ lesion of each group mice was cut, while the brain tissue of 5 remained normal mice mentioned in step 2.2 was cut. The samples were placed in 10% formaldehyde solution for fixing 24 h, and embedded with paraffin for making paraffin block, then dyed by immunohistochemistry analysis SP method. The immunohistochemical results were analyzed by semiquantitative method, and finally, the expression rate of LAG-3 protein in different tissue sample was subjected to statistical analysis.

(3) T Cell Proliferation Experiment

Current research indicated that LAG-3 is the inhibiting factor for proliferation of T lymphocytes, and can develop negative regulation on the proliferation of T lymphocytes, further produce a harmful effect on the prognosis of tumors, as well as promote the progression of tumors. Detecting the proliferation status of T lymphocytes may reflect the strong/weak inhibitory action of LAG-3. After finishing the experiment, the peripheral blood of each group mice was collected by removal of eyeballs, and high purity of CD3+T cells (>97%) were obtained using CD3 negative selection kit, that were dyed with LAG-3-PE, to determine the expression status of LAG-3.

3. Experimental Results 3.1 Pharmacodynamics Testing Results for Tumors

Figure 5:
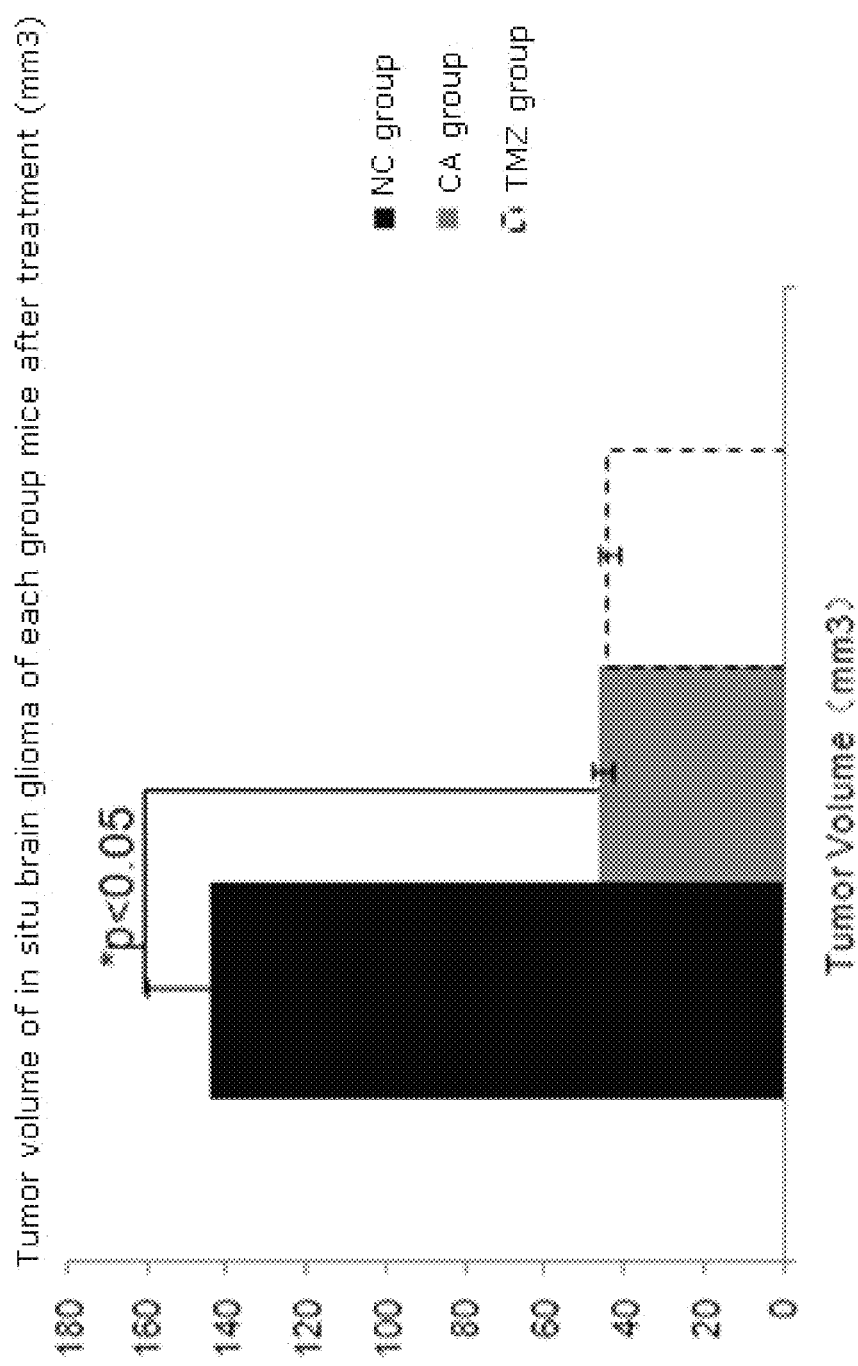
FIG. 5 shows the gross tumor volume after treating in situ brain glioma of each group mice in example 3.

Using mice with GL261 brain in situ glioma as models, the pharmacodynamics of treating brain glioma with chlorogenic acid freeze-dried powder injection was investigated. Results showed that compared with the saline control group, chlorogenic acid can effectively inhibit the growth of in situ lesion, with a significant difference (*$P<0.05$); while compared with positive drug temozolomide, their therapeutic effect was equivalent. Experimental results are shown in FIG. 5.

3.2 Immunohistochemical Experimental Results

Figure 6:
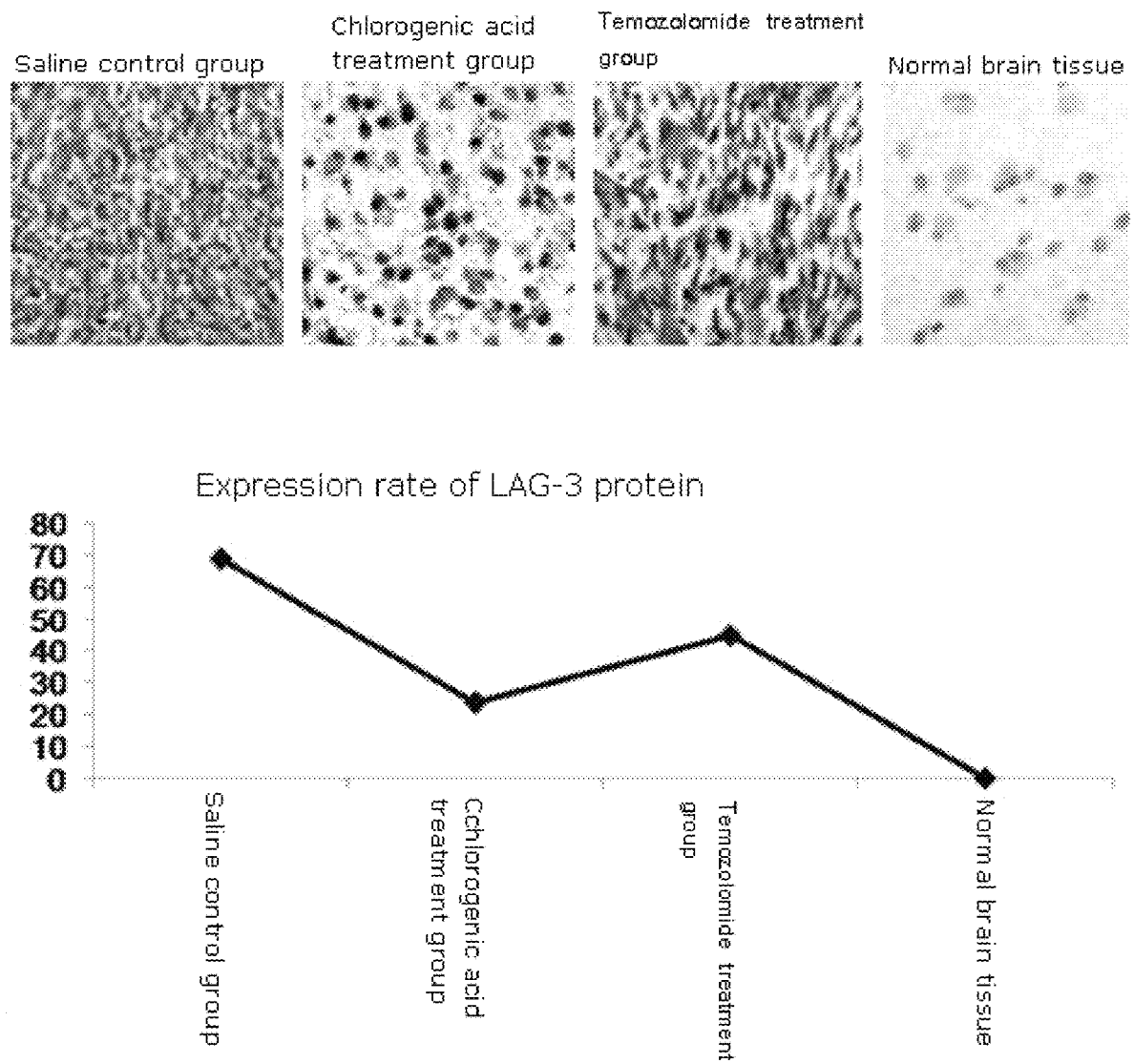
FIG. 6 shows immunohistochemistry results of LAG-3 protein expression in brain tissue of each group mice in example 3.

Immunohistochemical study on in situ lesion of each group mice was performed. Results showed that in the normal brain tissue, obvious expression of LAG-3 protein was not found; in the saline control group, the average percentage of LAG-3 protein high expression was 69%; while in chlorogenic acid treatment group, the average percentage of LAG-3 protein high expression was 23.78%; in temozolomide treatment group, the average percentage of LAG-3 protein high expression was 44.83%. Experimental results indicated that high expression of LAG-3 has a correlation with the therapeutic effect of tumors, and according to the tumor size, the tumor treatment effectiveness of chlorogenic acid powder injection and temozolomide was equivalent. However, based on the expression of LAG-3 protein, it was shown that chlorogenic acid can more greatly inhibit the expression of LAG-3 protein, and exert its anti-tumor action by inhibiting LAG-3. Experimental results are shown in FIG. 6.

3.3 Experimental Results of T Cell Proliferation

Figure 7:
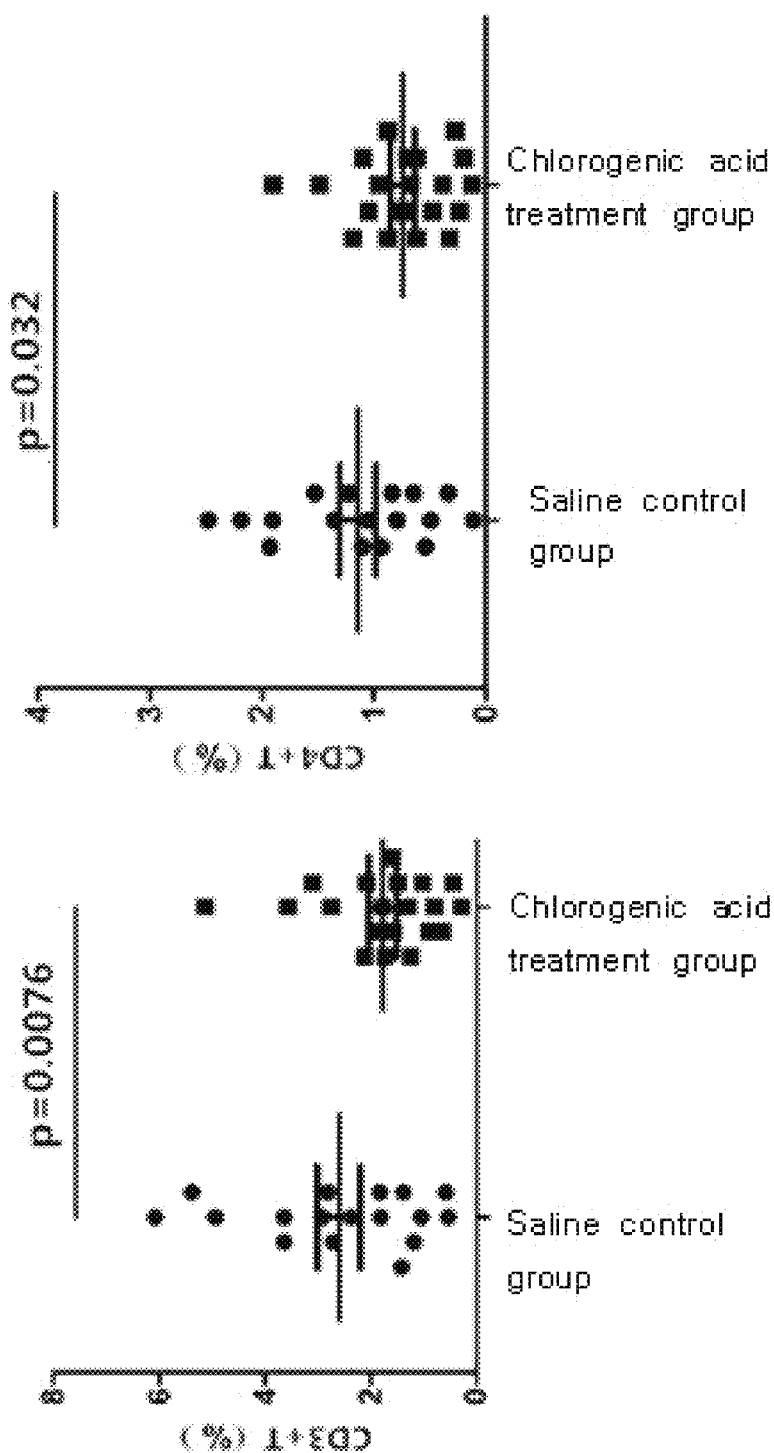
FIG. 7 shows the percentage of peripheral blood T lymphocytes in the saline control group and the chlorogenic acid treatment groups in example 3.

Current research indicated that LAG-3 is the inhibiting factor of T lymphocytes, and has a negative regulation on the proliferation of T lymphocytes. Inhibition on LAG-3 should produce a promotive effect on the proliferation of T lymphocytes. In this experiment, the percentage of CD3+T lymphocytes and CD4+T lymphocytes in peripheral blood lymphocytes of both the saline control group and the chlorogenic acid treatment group was determined. Results showed that compared with the saline control group, chlorogenic acid treatment group may obviously promote the proliferation of CD3+T lymphocytes and CD4+T lymphocytes. Experimental results are shown in FIG. 7.

The correlation of LAG-3 with tumor was mainly displayed by its ability to inhibit the proliferation of T lymphocytes, thus making the tumor develop immune tolerance and promoting the progress of tumors. In this example, GL261 in situ brain glioma mice were used as models, and based on investigating the pharmacodynamics of treating brain glioma with chlorogenic acid injection, the correlation of LAG-3 and tumors as well as peripheral blood T lymphocytes was further confirmed. It was determined that chlorogenic acid may inhibit the expression of LAG-3 in brain glioma, and this inhibitory effect was also obviously displayed in the proliferation of peripheral blood lymphocytes.

[Example 4] Investigation on the Pharmacodynamics and the Action Mechanism of Chlorogenic Acid Gastric Floating Tablets in In Vivo Chronic HBV Infection Mice 1. Experimental Animals and Materials 1.1 Experimental Animals Chronic hepatitis B model mice transfected with HBV virus, 18-22 g, 30 mice; normal balb/c mice, 18-22 g, 10 mice.

1.2 Experimental Materials

Flow cytometer, fluorescent quantitation PCR apparatus, etc.

2. Experimental Method 2.1 Preparation of Chlorogenic Acid Gastric Floating Tablets According to the formula shown in Table 6, 10 g chlorogenic acid crude drug, 50 g hydroxypropyl cellulose, 30 g stearic acid, 10 g sodium bicarbonate, 60 g microcrystalline cellulose, and 40 g lactose were weighed, and the crude and adjuvant materials were passed through 100 mesh sieve, then initially mixed by equal incremental method. The crude and adjuvant materials were further passed through 80 mesh sieve and thoroughly mixed, pressed to tablets with suitable hardness. The materials were granulated by pressing and passing through 20 mesh sieve, and then subjected to punch tableting, to obtain chlorogenic acid gastric floating tablets.

TABLE 6

Formula table of chlorogenic acid gastric floating tablets in example 4

| Ingredients | Content (wt %) | role |
| --- | --- | --- |
| Chlorogenic acid crude drug | 5 | Principal agent |
| Hydroxypropyl cellulose | 25 | Backbone agent |
| Stearic acid | 15 | Floating assistant agent |
| Sodium bicarbonate | 5 | Blowing agent |
| Microcrystalline cellulose | 30 | Bulking agent |
| lactose | 20 | Bulking agent |

2.2 Animal Grouping and Dosage Regimen

In this experiment, chronic hepatitis B model mice transfected with HBV virus were divided to 3 groups, 10 mice for each group, including the saline control group (NC group), hepatitis B immunoglobulin positive control group (HBVIG group) and chlorogenic acid gastric floating tablet treatment group (CA group), normal mice as the negative control group. The detailed grouping and the dosage regimen are shown in Table 7.

TABLE 7

Mice grouping and dosage regimen in example 4

| Group | Dosage | Administration times | Administration mode |
| --- | --- | --- | --- |
| Saline control group (NC group) | Same volume saline | 20 | Oral administration/intragastric administration |
| Chlorogenic acid gastric floating tablet treatment group (CA group) | 60 mg/kg | 20 | Oral administration/intragastric administration |
| Hepatitis B immunoglobulin positive control group (HB VIG group) | 9 IU/mouse | 2 | Intramuscular injection |
| Normal control group mice (N group) | Same volume saline | 20 | Oral administration/intragastric administration |

2.3 Detection of Alanine Aminotransferase (ALT) in Peripheral Blood of Mice

Alanine aminotransferase (ALT) has a direct correlation with the prognosis of hepatitis, and its content can reflect the therapeutic effect of drugs, thus in this experiment, the content of ALT in peripheral blood of each group mice at different time point after treatment was detected. Amongst, ALT was quantitatively measured by automatic biochemical analyzer, and by comparing the ALT value within treatment group as well as the ALT value of the treatment group with that of the control group at the same time point, the therapeutic effect of chlorogenic acid gastric floating tablet against hepatitis B was evaluated. In particular, on days 0, 4, 8, 12, 16, and 20 of this experiment, the peripheral blood was collected from caudal vein of mice, and the blood was used as the sample for measuring.

2.4 Determination of LAG-3 Distribution Frequency in Peripheral Blood of Mice

In order to further confirm the relationship between the therapeutic effect and LAG-3, as well as identify the action target of chlorogenic acid being LAG-3, in this experiment, LAG-3 distribution frequency in peripheral blood of each group mice at therapeutic terminal point was detected, that is said, on the second day after completion of experiment (i.e. day 21 of experiment), the peripheral blood of mice was collected by removal of eyeballs, and then the expression status of LAG-3 in peripheral blood of each group mice was detected by flow cytometer.

Figure 8:
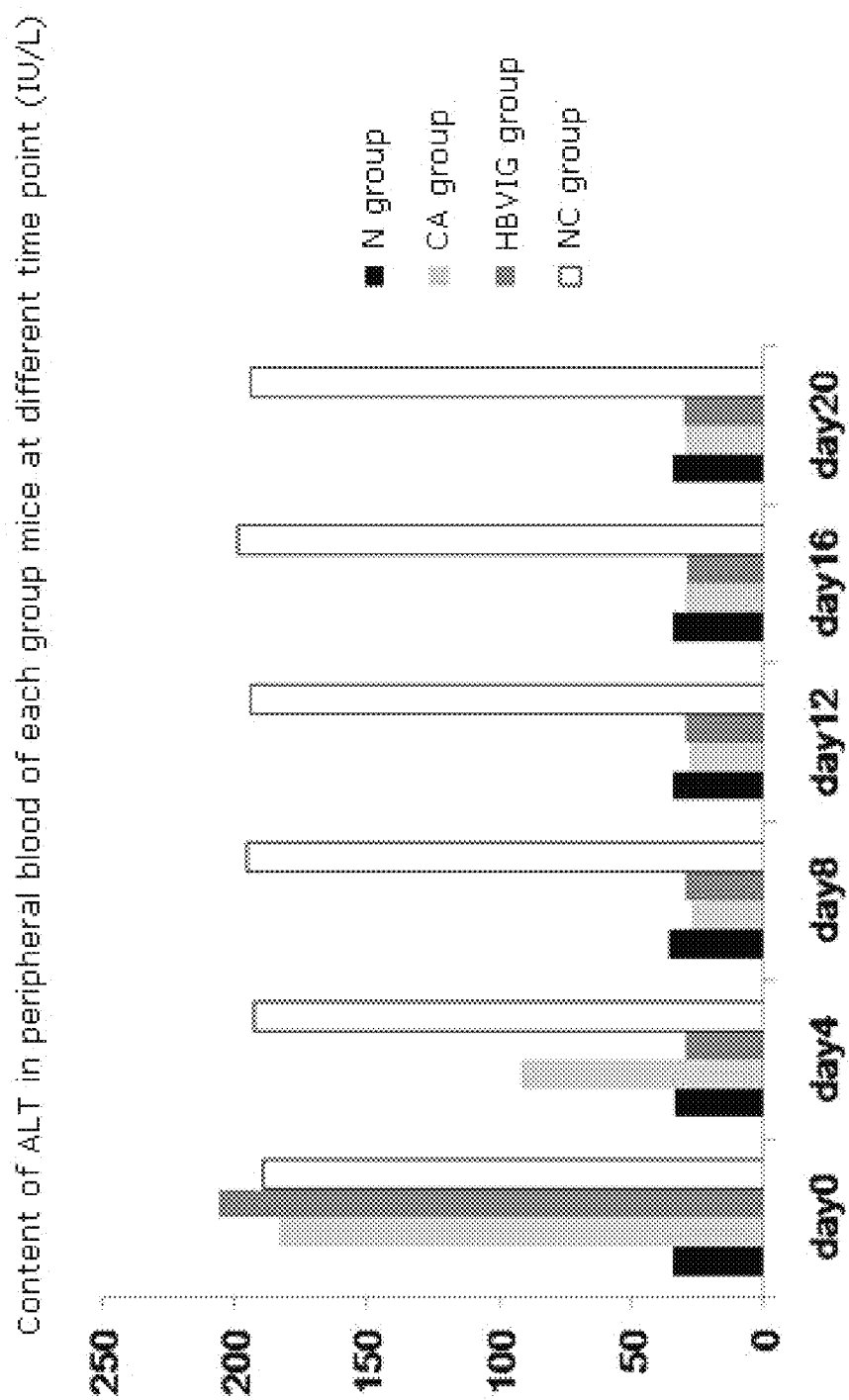
FIG. 8 shows the ALT content in peripheral blood of each group mice at different time point in example 4.

3. Experimental Results 3.1 Preparation of Chlorogenic Acid Gastric Floating Tablets 3.2 Detection of ALT in Peripheral Blood of Mice In this experiment, the content of ALT in peripheral blood of each group mice at different time point was follow-up detected. Results showed that compared with mice of control group (NC group), the content of ALT in control group of chronic hepatitis B model mice transfected with HBV virus (NC group) was obviously increased, proving the chronic hepatitis B model mice transfected with HBV virus have the typical characteristics of this disease. Chlorogenic acid gastric floating tablets and HBIG can both significantly reduce the content of ALT in peripheral blood of mice in corresponding treatment group, i.e. compared with NC group, CA group and HBIG group were significantly different, confirming that chlorogenic acid can obviously reduce the content of ALT in peripheral blood. The experimental results are shown in FIG. 8.

[Example 5] Investigation on Therapeutic Effect of Chlorogenic Acid Gastric Floating Tablet Against Sepsis of Mice 1. Experimental Method 1.1 Establishment of Sepsis Mouse Model Establishing sepsis mouse model by CLP operation, 30 mice; 10 normal balb/c mice.

1.2 Experimental Materials and Apparatus

Flow cytometer, LAG-3 (CD223)-PE antibody, CD8-PE-Cy7 antibody, CD4-APC antibody, etc.

2. Experimental Method 2.1 Animal Grouping and Dosage Regimen 30 sepsis model mice were randomly divided to 3 groups, 10 mice for one group, including model mice control group (NC group), chlorogenic acid gastric floating tablet treatment group (CA group), and LAG-3 antibody treatment group (LAG3IG group), and in addition, 10 normal balb/c mice were the negative control group (N group). Amongst, LAG3IG group received intramuscular injection on days 1 and 3 of experiment, while CA group receives intraperitoneal injection every day, for 7 days successive administration. NC group and N group orally took the same volume of saline as that of CA group. From the begin to day 10 of experiment, the survival rate and the live time of mice were recorded. On day 10 of experiment, the eyeballs of all mice were removed for collecting blood, that was equally divided to two parts for use. The detailed grouping and the dosage regimen are shown in Table 8.

TABLE 8

Experimental grouping and dosage regimen for pharmacodynamics investigation on sepsis mice in example 5

| Group | dosage | Administration times | Administration mode |
|---|---|---|---|
| Saline control group (NC group) | Same volume of saline | 7 | Oral administration/intragastric administration |
| Chlorogenic acid gastric floating tablet treatment group (CA group) | 60 g/kg | 7 | Oral administration/intragastric administration |
| LAG-3 monoclonal antibody group (LAG3IG group) | 10 IU/mouse | 2 | Intramuscular injection |
| Normal control group mice (N group) | Same volume of saline | 20 | Oral administration/intragastric administration |

2.2 Determination of the Expression Status of LAG-3 on the Surface of CD4+T Lymphocytes and CD8+T Lymphocytes in the Peripheral Blood of Mice LAG-3 is the inhibitory molecule present in T lymphocyte, and can produce obvious effect on it. One part of whole blood collected in step 2.1 was taken, and to each tube, were added anti-mouseCD8-PE-Cy7 and anti-mouseCD4-APC and Anti-MouseLAG-3 (CD223)-PE-fluorscein labeled monoclonal antibody (each 1M1), then 100 µL blended blood was respectively added to each tube. Reagents and blood were mixed by low velocity vortex for 3 s, then they were allowed to react at room temperature by protecting from light for 20 min. After that, 2 mL red blood cell lysate was added, and placed at room temperature under away from light for 15 min. The mixture was further washed 2 times with PBS, and measured using flow cytometer.

Figure 9:
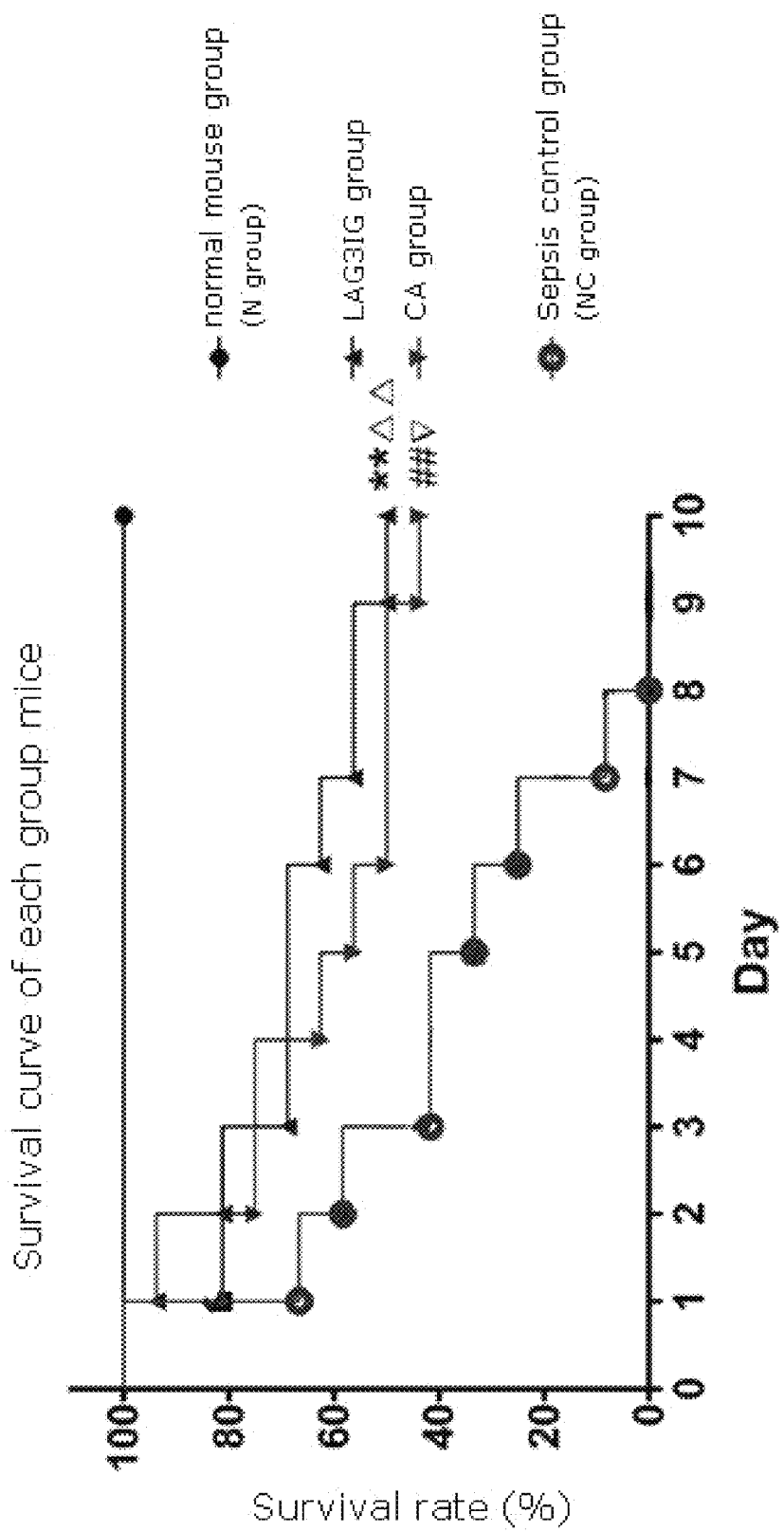
FIG. 9 shows the investigation on the survival rate and the childbirth time in pharmacodynamics experiment of mice with sepsis in example 5.

3. Experimental Results 3.1 Investigation Results on the Survival Rate and the Live Time of Mice During experiment, the survival rate and the live time of each group mice were recorded. Results were as follows: sepsis model mice were all dead before completion of experiment, while compared with the sepsis control group, the survival rate and the live time of mice in LAG3IG group and CA group were obviously improved. Experiment showed that chlorogenic acid gastric floating tablets (CA group) had a positive therapeutic effect on the sepsis of mice, and can improve the survival rate and elongate the live time. Experimental results are shown in FIG. 9.

3.2 The Expression Status of LAG-3 in Peripheral Blood Lymphocytes of Mice

Figure 10A:
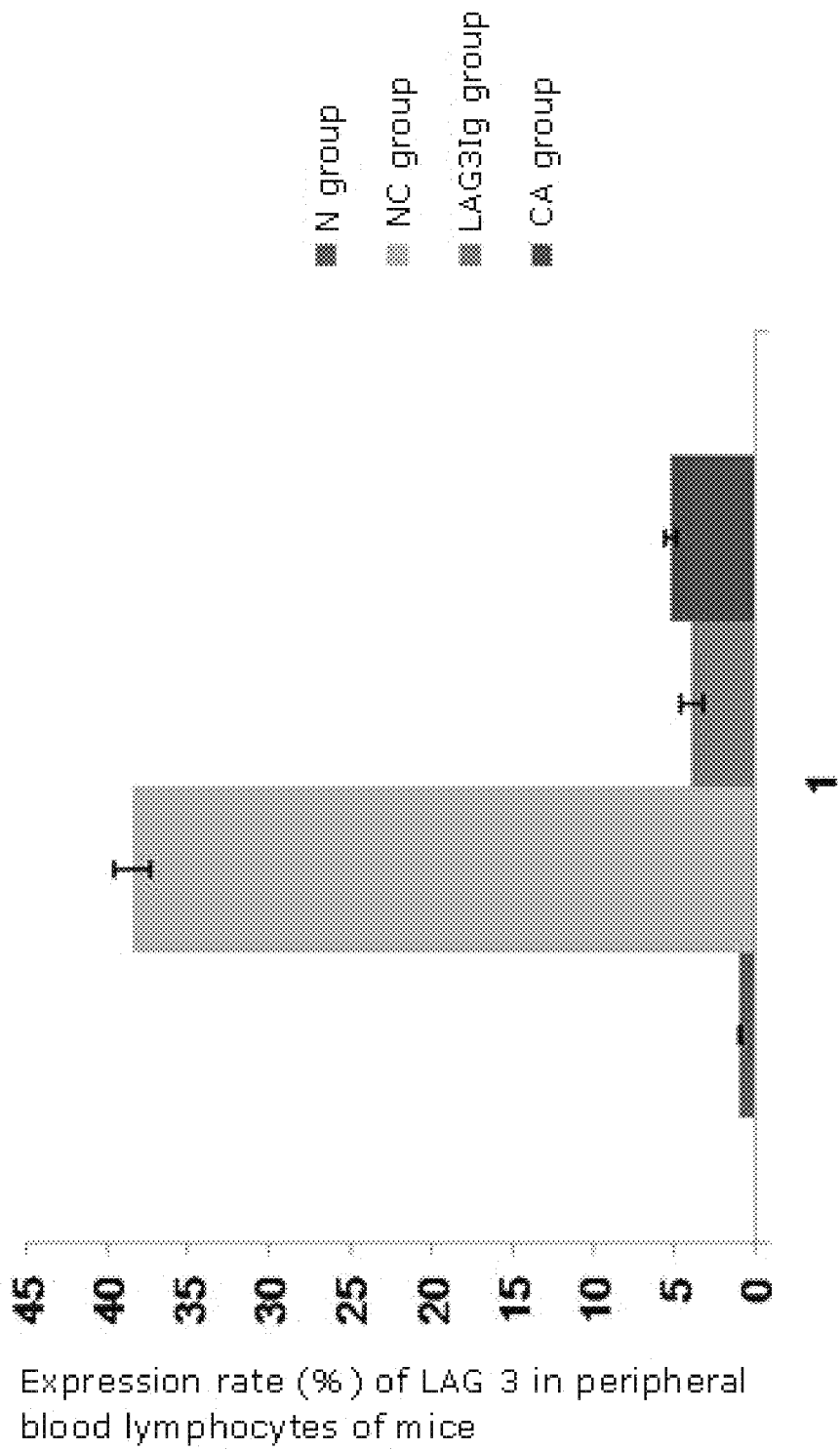
FIG. 10a shows the LAG-3 expression rate in peripheral blood lymphocytes of mice in example 5.
Figure 10B:
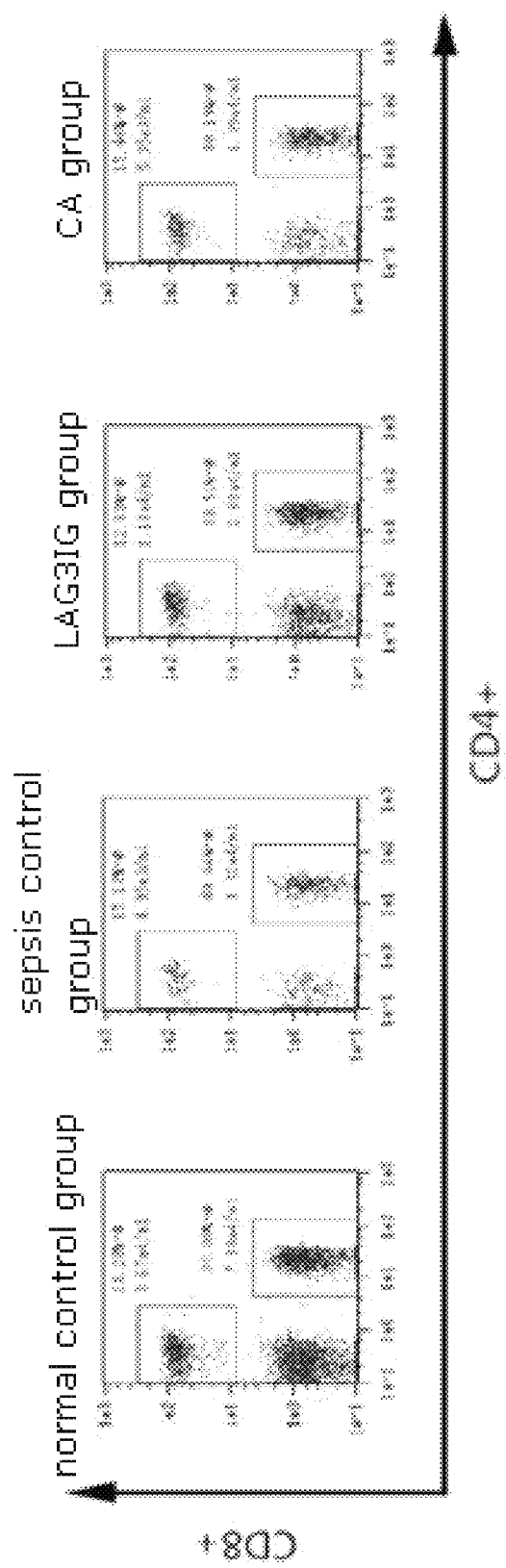
FIG. 10b shows the ratio of CD4+T and CD8+T in peripheral blood of mice in example 5.

The detection results of expression of LAG-3 in peripheral blood lymphocytes of each group mice showed that the expression level of LAG-3 in normal control group (N group) was lower (10a), and the amount of corresponding CD4+T and CD8+T lymphocytes was normal (FIG. 10b); while for mice in the sepsis model control group (NC group), the expression of LAG-3 was obviously increased (FIG. 10a), and the amount of corresponding CD4+T and CD8+T lymphocytes obviously decreased (FIG. 10b). After treatment with LAG3IG and chlorogenic acid gastric floating tablets, compared with the model control group (NC group), the expression of LAG-3 in mice with sepsis was obviously decreased (FIG. 10a), and the amount of corresponding CD4+T and CD8+T lymphocytes also obviously proliferated (FIG. 10b). The detailed experimental results are shown in FIG. 10a and FIG. 10b.

In this example, considering the correlation of LAG-3 target and sepsis, using LAG-3 antibody as positive control, the therapeutic effect of chlorogenic acid gastric floating tablets on the sepsis of mice was investigated, and results showed that chlorogenic acid has an obvious curative effect on the sepsis of mice. Moreover, this effect was displayed by the active suppression of LAG-3 target on the surface of peripheral blood lymphocytes of mice, and correspondingly, CD4+T and CD8+T lymphocytes in peripheral blood had an obvious proliferation. That further indicated that chlorogenic acid can treat LAG-3 related sepsis by inhibiting LAG-3 target.

[Example 6] Preparation of Chlorogenic Acid Powder

Chlorogenic acid was obtained by extraction and purification from *Eucommina ulmoides* leaves, with a purity of 98.82%.

1000 g chlorogenic acid was aseptically subpackaged as the powder at 1000 mg/bottle or 1000 mg/bag. In conclusion, the present invention found the inhibitory effect of chlorogenic acid on LAG-3 target, and chlorogenic acid can be used for treatment of diseases with LAG-3 as target, such as anti-cancer, anti-virus, sepsis, etc. Furthermore, chlorogenic acid can be prepared as gastric floating tablets by suitable methods, for further improving the oral bioavailability of chlorogenic acid.

The present invention is not limited to above-mentioned specific examples. The present invention can be expanded to any new feature disclosed in the specification or any new combination thereof, as well as to any new method or step in the process disclosed or any new combination thereof.

[Example 7] Preparation of Chlorogenic Acid Freeze-Dried Powder Injection

Chlorogenic acid was obtained by extraction and purification from *Eucommina ulmoides* leaves, with a purity of 99.5%.

30 g chlorogenic acid, 80 g mannitol, and 2 g sodium bisulphite were completely dissolved in the water for injection, filtered, filled, and lyophilized to prepare 30 mg/branch chlorogenic acid freeze-dried powder injection.

The invention claimed is:

1. A method for inhibiting Lymphocyte activating gene 3 (LAG-3) activity and LAG-3 expression in a subject in need thereof, comprising administering an effective amount of a pharmaceutical composition to the subject, wherein:
the pharmaceutical composition comprises chlorogenic acid and is in the form of gastric floating tablets;
the chlorogenic acid is administered at a dosage of 10-60 mg/kg per day; and
diseases treatable by inhibiting LAG-3 comprises chronic hepatitis B.

2. The method according to claim 1, wherein the pharmaceutical composition comprises further comprises pharmaceutically acceptable adjuvants.

3. The method according to claim 1, wherein the gastric floating tablets are prepared by using chlorogenic acid as principal agent, hydroxypropyl cellulose as backbone materials, stearic acid as floating assistant, sodium bicarbonate as foaming agent, and microcrystalline cellulose and lactose as bulking agent.

4. A method for treating chronic hepatitis B, comprising administering an effective amount of a pharmaceutical composition to a subject in need thereof, wherein:
the pharmaceutical composition comprises chlorogenic acid;
the chlorogenic acid is in in the form of gastric floating tablets and inhibits LAG-3 activity and LAG-3 expression; and
the chlorogenic acid is orally administered at a dosage of 5 mg/kg per day.

* * * * *

SEQUENCE LISTING

<160> NUMBER OF SEQ ID NOS: 2

<210> SEQ ID NO 1
<211> LENGTH: 27
<212> TYPE: DNA
<213> ORGANISM: artificial sequence
<220> FEATURE:
<223> OTHER INFORMATION: Forward primer for LAG-3 sequence

<400> SEQUENCE: 1
ctagctagca gcgagctcct tccagtc                                     27

<210> SEQ ID NO 2
<211> LENGTH: 27
<212> TYPE: DNA
<213> ORGANISM: Artificial Sequence
<220> FEATURE:
<223> OTHER INFORMATION: Reverse primer for LAG-3 sequence

<400> SEQUENCE: 2
gactggaagg agctcgctgc tacgtag                                     27